(12) United States Patent
Chun (10) Patent No.: US 6,383,798 B1
(45) Date of Patent: May 7, 2002

(54) METHOD FOR SELECTING DESICCATION TOLERANT STRAINS OF BACTERIA

(75) Inventor: Wesley W. C. Chun, Moscow, ID (US)

(73) Assignee: Idaho Research Foundation, Inc., Moscow, ID (US)

( * ) Notice: Subject to any disclaimer, the term of this patent is extended or adjusted under 35 U.S.C. 154(b) by 0 days.

(21) Appl. No.: 09/595,693

(22) Filed: Jun. 16, 2000

Related U.S. Application Data (62) Division of application No. 09/348,438, filed on Jul. 7, 1999, now Pat. No. 6,156,560.

(51) Int. Cl.$^7$ .............................................. C12N 1/20
(52) U.S. Cl. .................... 435/253.3; 435/243; 435/248; 435/252.1
(58) Field of Search ................................ 435/243, 248, 435/252.1

(56) References Cited

U.S. PATENT DOCUMENTS

| | | |
|---|---|---|
| 5,244,658 A | 9/1993 | Parke |
| 5,264,210 A | 11/1993 | Novitski et al. |
| 5,348,742 A | 9/1994 | Howell et al. |
| 5,552,315 A | 9/1996 | Slininger et al. |
| 5,783,411 A | 7/1998 | Schisler et al. |

FOREIGN PATENT DOCUMENTS

| EP | 0 742 494 A2 | 2/1992 |
|---|---|---|

OTHER PUBLICATIONS

Sutra et al., Taxonomy of Pseudomonas Strains Isolated from Tomato Pith Necrosis: Emended Description of *Pseudomonas corrugata* and Proposal of Three Unnamed Fluorescent Pseudomonads Genomospecies, *Int. J. Baceriol*, vol. 47, No. 4 (Oct. 1997), pp. 1020–1033.
PCT/US 00/ 14485 International Search Report.
Arthur Kelman, Phytopathology, *The Relationship of pathogenicity in Pseudomonas Solanacearum to Colony Appearance on a Tetrazolium Medium*, 1954, vol. 44, pp. 693–695.
Patricia Broadbent, et al, Phytopathology, *Effect of Bacillus spp. on Increased Growth of Seedlings in Steamed and in Nontreated Soil*, 1977, vol. 67, pp. 1027–1032.
C.M. Scarlett et al, Ann. Appl. Biol., *Tomato pith necrosis caused by Pseudomonas corrugatoa n.sp.*, 1978, vol. 88, pp. 105–119.
J.W. Kloepper, M.N. Schroth, I.S.P.P., Phytobacteriology Section, *Plant Growth Promoting Rhizobacteria on Radishes*, 1978, pp. 879–882.
F.L. Lukezie, Phytopathology, *Pseudomonas corrugata, a Pathogen of Tomato Isolated from Symptomless Alfalfa Roots*, 1979, vol. 69, pp. 27–31.
J.W. Kloepper, Phytopathology, *Effect of Seed Piece Inoculation with Plant Growth–Promoting Rhizobacteria on Populations of Erwinia carotovora on Potato Roots and in Daughter Tubers*, 1983, vol. 73, pp. 217–219.

G.–W. Xu and D.C. Gross, Phytopathology, *Selection of Fluorescent Pseudomonads Antagonistic to Erwinia carotovora and Suppressive of Potato Seed Piece Decay*, 1986, vol. 76, pp. 414–422.
David M. Weller, Ann. Rev. Phytopathol., *Biological Control of Soilborne Plant Pathogens in the Rhizosphere with Bacteria*, 1988, vol. 26, pp. 379–407.
Marco Scortichini, Physopathology, *Occurrence in Soil and Primary Infections of Pseudomonas corrugata Roberts and Scarlett*, 1989, vol. 125, pp. 33–40.
Marta Herrero et al, Journal of Bacteriology, *Transposon Vectors Containing Non–Antibiotic Resistance Selection Markers for Cloning and Stable Chromosomal Insertion of Foreign Genes in Gram–Negative Bacteria*, 1990, vol. 172, pp. 6557–6567.
J.L. Parke et al, Plant Disease, *Biological Control of Pythium Damping–Off and Aphanomyces Root Rot of Peas by Application of Pseudomonas cepacia or P. fluorescens to Seed*, 1991, vol. 75, pp. 987–992.
T.J. McLoughlin et al, American Society for Microbiology, *Pseudomonas cepacia Suppression of Sunflower Wilt Fungus and Role of Antifungal Compounds in Controlling the Disease*, 1992, vol. 58, pp. 1760–1763.
Angela R. DeLaCruz et al, American Society for Microbiology, *Biological Suppression of Potato Ring Rot by Fluorescent Pseudomonads*, 1992, vol. 58, pp. 1986–1991.
M.H. Ryder and A.D. Rovira, Soil Biol. Biochem, *Biological Control of Take–All of Glasshouse–Grown Wheat Using Strains of Pseudomonas corrugata Isolated from Wheat Field Soil*, 1993, vol. 25, pp. 311–320.
T. Zhou and T.C. Paulitz, Phytopathology, *In Vitro and in Vivo Effects of Pseudomonas spp. on Pythium aphanidermatum: Zoospore Behavior in Exudates and on the Rhizoplane of Bacteria–Treated Cucumber Roots*, 1993, vol. 83, pp. 872–876.
M.M. Lopez et al, Plant Pathology, *Characterization of Spanish Isolates of Pseudomonas corrugata from Tomato and Pepper*, 1994, vol. 43, pp. 80–90.
D.A. Schisler et al, Plant Disease, *Selection and Performance of Bacterial Strains for Biologically Controlling Fusarium Dry Root of Potatoes Incited by Gibberalla Pulicaris*, 1994, vol. 78, pp. 251–255.
Chun and Shetty, Phytopathology, *Control of silver scarf disease of potatoes caused by Helminthosporium Solani Dur. & Mont. with Pseudomonas corrugata*, 1994, vol. 84, p. 1090.
Daqun Liu et al, Phytopathology, *Biological Control of Potato Scab in the Field with Antagonistic Streptomyces scabies*, 1995, vol. 85, pp. 827–831.

(List continued on next page.)

Primary Examiner—Francisco Prats
Assistant Examiner—Susan D. Coe
(74) Attorney, Agent, or Firm—Senniger, Powers, Leavitt & Roedel (57) ABSTRACT

The present invention pertains to a method of identifying and selecting desiccation tolerant strains of bacteria and a method of producing a desiccated formulation of the identified strains.

11 Claims, 2 Drawing Sheets

OTHER PUBLICATIONS

J.M. Lorang et al, Phytopathology, *Identification of Potato Scab Inducing and Suppressive Species of Streptomyces*, 1995, vol. 85, pp. 261–268.

P. Vidhyasekaran and M. Muthamilan, Plant Disease, *Development of Formulations of Pseudomonas Fluorescens for Control of Chickpea Wilt*, 1995, vol. 79, pp. 782–786.

D.C. Thomas et al, Plant Disease, *Evaluation of Bacterial Antagonists for Reduction of Summer Patch Symptoms in Kentucky Bluegrass*, 1996, vol. 80, pp. 856–862.

Wesley Chun, Recent Research Developments in plant Pathology, *The Use of Phytopathogenic Bacteria as Biological Control Agents*, 1996, vol. 1, pp. 113–121.

B. Cottyn et al, Plant Disease, *Bacterial Diseases of Rice. II. Characterization of Pathogenic Bacteria Associated with Sheath Rot Complex and Grain Discoloration of Rice in the Philippines*, 1996, vol. 80, pp. 438–445.

Fanny Rodriguez and William F. Pfender, Phytopathology, *Antibiosis and Antagonism of Sclerotinia Homoeocarpa and Drechslera poae by Pseudomonas Fluorescens Pf–5 In Vitro and In Planta*, 1997, vol. 87, pp. 614–621.

M.C. Emanuele, FEBS Letters, *Corpeptins, New Bioactive Lipodepsipeptides from Cultures of Pseudomonas corrugata*, 1998, vol. 433, pp. 317–320.

W. Chun, G. Yong, K. Kettle, *The Potential Use of Pseudomonas corrugata for Biological Control of Fungal and Bacterial Diseases of Plants*, Phytopathology, 1993, vol. 83, No. 12, pp. 1339.

W. Chun, K. Shetty, *Control of Silver Scurf Disease of Potatoes Caused by Helminthosporium Solani Dur. & Mont. With Pseudomonas corrugata*, Phytopathology, 1993, vol. 83, pp. 1339.

W. Chun and Y. Gao, *Suppression of Pythium Root Rot of Wheat by Pseudomonas corrugata*, Phytopathology, 1995, vol. 85, No. 10, pp. 1146.

K.L. Schroeder, W. Chun, *Pseudomonas corrugata Pathogenicity in Tomatoes and Antagonism of Clavibacier Michiganensis subsp. sepedonicus in Potato Plants are Unlinked Trails*, 1997, Phytopathology, vol. 87, No. 6, p. 587.

W. Chun, A.R. Poplawsky, H. Nair, *Suppression of Pea Root Diseases by Pseudomonas corrugata*, 1998, Phytopathology, vol. 88, No. 9, p. 517.

METHOD FOR SELECTING DESICCATION TOLERANT STRAINS OF BACTERIA

CROSS-REFERENCE TO RELATED APPLICATIONS

This application is a divisional application of U.S. application Ser. No. 09/348,438, filed Jul. 7, 1999, now U.S. Pat. No. 6,156,560, issued Dec. 5, 2000, and herein incorporated by reference in its entirety.

GOVERNMENT INTERESTS

This invention was made with Government support under contract number 95-34239-1418 awarded by the United States Department of Agriculture. The Government has certain rights in this invention.

FIELD OF THE INVENTION

The present invention pertains to novel strains of *Pseudomonas corrugata* and uses of the strains in biological control against soil-borne pathogens of plants. Also encompassed by this invention is a method of identifying and selecting desiccation tolerant strains of bacteria and a method of producing the desiccated formulations of the identified strains.

BACKGROUND OF THE INVENTION

Bacterial and fungal pathogens can result in significant yield losses or decrease the market quality of agricultural crops. Under favorable conditions, soil resident fungal pathogens may decrease seedling emergence, cause root rots, or reduce plant vigor. Many fungal pathogens produce spores that aid both dispersal and survival of the fungus. Bacteria, are single-celled organisms that generally do not produce spores. Many bacterial pathogens depend on host material for survival. Other bacterial pathogens may be able to survive in the soil as saprophytes.

For both types of pathogens, entry into plant tissue is required for the production of disease symptoms. Prevention of pathogen entry would significantly decrease the likelihood of disease. Chemical seed treatment with fungicides can be used to provide economical protection against some soil-borne fungal pathogens. Antagonistic bacteria may also be used to provide biological control protection against undesirable pathogens. However, biological control bacteria must be able to survive drying to be readily employed as a seed treatment. Additionally, compatibility with fungicides would enable the combination of biological controls with chemicals to achieve disease control.

Crops are susceptible to a variety of different pathogens. For example, peas are susceptible to a variety of root-infecting fungi (*Aphanomyces euteiches, Fusarium oxysporum* f. sp. *pisi, F.solani* f. sp. *pisi,* and *Sclerotinia sclerotiorum*). Several Pythium species (*P. debaryanum, P. ultimum, P. splendens, P. aphanidermatum,* and *P. irregulare*) are known to cause damping-off and root rot in peas. Many of these same pathogens are pathogenic on potato. Peas and potatoes are also known hosts for the bacterial leaf spot pathogen, *Pseudomonas pisi,* and the bacterial ring rot pathogen, *Clavibacter michiganensis* subsp. *sepedonicus,* respectively.

*Aphanomyces euteiches* (the causal agent of Aphanomyces root rot) by far is the most serious disease threat to pea production. The fungus produces sporangia that release many motile zoospores that "swim" to susceptible root tissue. Infection occurs after zoospores encyst and form germ tubes that penetrate the epidermis of young roots. The fungus also produces thick-walled oospores that are the primary overwintering structures. These spores may germinate directly or form sporangia in the presence of young pea plants. Oospores of *A. euteiches* have been know to survive for as long as 20 years in the soil in the absence of any crops. At present no chemical control is available and resistant cultivars are lacking. Cool moist conditions that normally exist as the seeds germinate are optimal conditions for this pathogen. Thus, alternative methods are needed to manage this disease.

Ring rot disease caused by *Clavibacter michiganensis* subsp. *sepedonicus* is a major concern in potato seed production. The bacterium's ability to survive on tools, equipment, dried infected plant material, volunteer plants, insects and alternative hosts has made eradication impossible. Furthermore, the pathogen may escape detection during field surveys and seed tests as symptoms are not always expressed in infected plants and tubers. Disease control ultimately rests on the accurate and sensitive detection of the bacterial ring rot pathogen. While disease incidence is low, presence of the disease results in rejection of the crop and loss of the field for five to seven years. Chemical control and resistant cultivars are not available for control of this disease.

Silver scurf is a post-harvest disease of potato tubers. Infection occurs in the field from inoculum carried on seed potatoes. In storage bins, lesions on the potato surface appear. This results in a significant decrease in quality as well as moisture loss by tubers. Recently strains have developed that are resistant to current fungicides.

Several different bacteria have been used as biological control agents for fungal diseases (Weller, 1988). The majority of antagonistic bacteria isolated from soil that displayed antagonistic properties were fluorescent pseudomonads (de la Cruz et al., 1992; Kloepper, 1983; Kloepper and Schroth, 1978; Liu et al., 1995; Lorang et al., 1995; McLoughlin et al., 1992; Rodriguez and Pfender, 1997; Thompson et al., 1996; Vidhyasekaran and Muthamilan, 1995.; Weller, 1988; Xu and Gross, 1986; Zhou and Paulitz, 1993). Other studies have shown that Gram positive bacteria such as Streptomyces and Bacillus may have some promise (Broadbent et al., 1977; Crawford, 1996; Liu et al., 1995; Lorang et al., 1995). However, phytopathogenic bacteria have not been extensively evaluated as biological control agents. *Burkholderia cepacia* (*Pseudomonas cepacia*) has been used in such studies (Parke, 1992; Parke et al., 1991). In some instances, *B. cepacia* strains used were obtained from soil and were not pathogenic on plants (Novitski et al., 1993).

*Pseudomonas corrugata* was first reported as a pathogen of tomatoes causing a necrosis of the pith (Scarlett et al., 1978). This bacterium has also been reported as a pathogen of rice (Cottyn et al., 1996) and pepper (Lopez et al., 1994). *P. corrugata* may be more widely present in agricultural soils (Schisler and Slininger, 1994; Scortichini, 1989) and has been isolated from alfalfa (Lukezic, 1979) and wheat (Ryder and Rovira, 1993) roots.

Since the host range of *P. corrugata* appears to be limited to tomato, pepper and possibly rice, wild-type isolates could be used on non-susceptible crops. Soil-borne isolates were recovered as antagonists of the potato scab pathogen, Streptomyces scabies (Schisler and Slininger, 1994). Other isolates have been found on wheat roots and have been used to suppress take-all disease of wheat (Ryder and Rovira, 1993). Additionally, suppression of Pythium root rot on cucumber was obtained by root treatment with *P. corrugata* (Zhou and Paulitz, 1993).

What is still needed is alternative biological control methods and agents against plant diseases, particularly for diseases where chemical control agents or resistant cultivars are unavailable or undesirable.

SUMMARY OF THE INVENTION

The present invention pertains to novel strains of *Pseudomonas corrugata* and the use of the strains in biological control against soil-borne pathogens of plants. A number of these strains are shown to be effective in reducing or controlling soil-borne pathogens of plants, including, but not limited to peas, potatoes and wheat. In particular the present invention pertains to 3 strains of *Pseudomonas corrugata* herein referred to as 0782-6, 0683-32 and 1090-11. *P. corrugata* isolates 0782-6 and 0683-32 have been identified as having the strongest antimicrobial activity to a variety of plants. Isolate 1090-11 showed little or no antifungal activity.

The *P. corrugata* strains may be formulated with a variety of delivery media to produce bacterial inocula, that may be used as either a dry powder or liquid suspension. The formulations may be introduced into the soil or may be applied to seeds, plant surfaces or portions of plants, such as roots, stems, leaves, and fruit, or plant parts may be dipped into the formulations, to treat the plants.

Also encompassed by this invention is a method of identifying and selecting desiccation tolerant strains of bacteria and a method of producing the desiccated formulations of the identified strains. The method comprises, in general, culturing the bacteria in a minimal nutrient broth medium containing a single carbon source (MMSC) for a minimum of approximately 24 hours. After the culturing of the bacteria for 24 hours, samples of the MMSC cultures are dried. The dried samples are then rehydrated, and plated on a complete nutrient substrate. The next step comprises identifying which strains have a high rate of survival by comparing the rate of survival of the rehydrated samples to the rate of survival of the bacteria cultured in the same minimal nutrient broth and selecting the strains having a high rate of survival. This process is repeated until no increase in survival is observed. In the case of the novel strains of *Pseudomonas corrugata* of the present invention, the composition comprising the desiccated strains and delivery medium has a long shelf life and is suitable for delivering the bacteria to plants for effective control of plant pathogens.

DETAILED DESCRIPTION OF THE INVENTION

Figure 1:
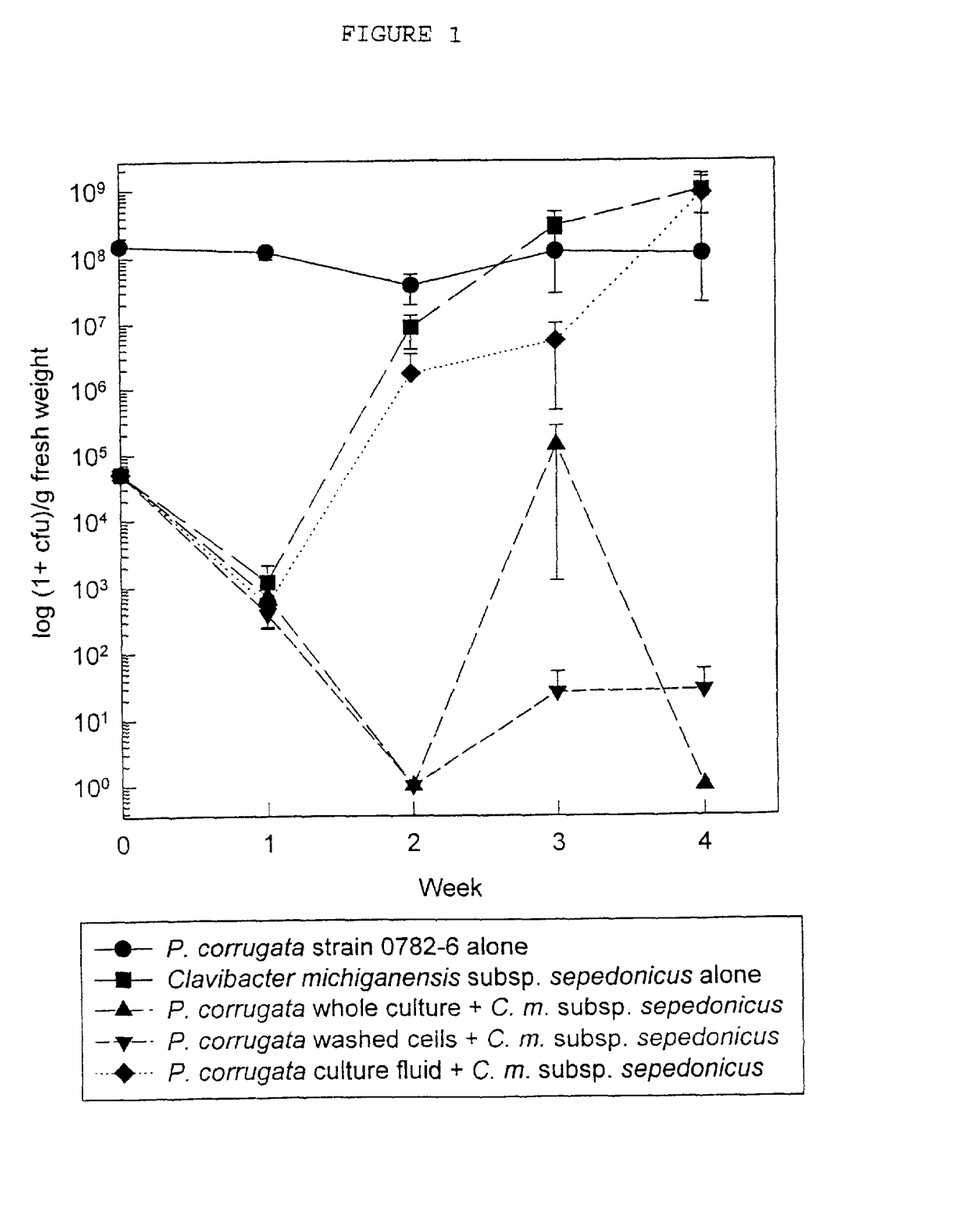
FIG. 1 is a graph showing suppression of *Clavibacter michiganensis* subsp. *sepedonicus* isolate CIC64S in eggplants with whole cultures, washed cells, and cell-free culture media of *Pseudomonas corrugata*. Error bars represent one standard error of the mean calculated from three replicate plants.
Figure 2:
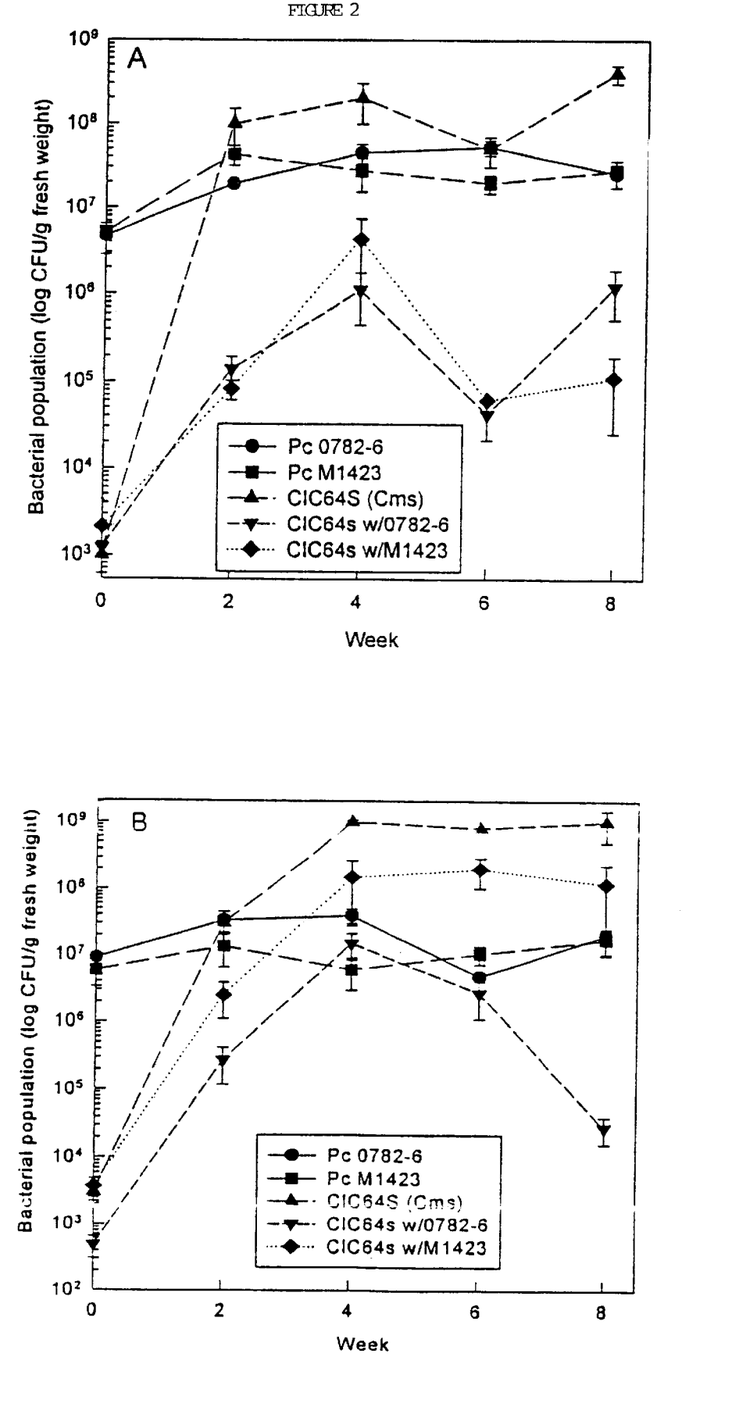
FIG. 2a is a graph showing suppression of Clavibacter populations in stems of Shepody potato plants by a wild type (0782-6) and a non-pathogenic (to tomatoes) mutant (M1423). Error bars represent one standard error of the mean of four replicate plants.
FIG. 2b is a graph showing suppression of Clavibacter populations in stems of Russet Burbank potato plants by a wild type (0782-6) and a non-pathogenic (to tomatoes) mutant (M1423). Error bars represent one standard error of the mean of four replicate plants.

The present invention pertains to novel strains of *Pseudomonas corrugata* and the use of the strains in biological control against soil-borne pathogens of plants. A number of these strains are shown to be effective in reducing or controlling soil-borne pathogens of plants, including, but not limited to peas, potatoes and wheat. In particular the present invention pertains to 3 strains of *Pseudomonas corrugata* herein referred to as 0782-6, 0683-32 and 1090-11. *P. corrugata* isolates 0782-6 and 0683-32 have been identified as having strong antimicrobial activity to a variety of plant pathogens. Isolate 1090-11 showed little or no antifungal activity.

As used herein, *Pseudomonas corrugata* 0782-6 means a strain of *Pseudomonas corrugata* deposited in accordance with the Budapest Treaty on the International Recognition of the Deposit of Microorganisms for the Purpose of Patent Procedure, on Mar. 4, 1999, at American Type Culture Collection (ATCC), 10801 University Blvd., Manassas, Va. 20110-2209, USA, and having the designation ATCC 202201.

As used herein, *Pseudomonas corrugata* 0683-32 means a strain of *Pseudomonas corrugata* deposited in accordance with the Budapest Treaty on the International Recognition of the Deposit of Microorganisms for the Purpose of Patent Procedure, on Mar. 4, 1999, at American Type Culture Collection (ATCC), 10801 University Blvd., Manassas, Va. 20110-2209, USA and having the designation ATCC 202203.

As used herein, *Pseudomonas corrugata* 1090-11 means a strain of *Pseudomonas corrugata* deposited in accordance with the Budapest Treaty on the International Recognition of the Deposit of Microorganisms for the Purpose of Patent Procedure, on Mar. 4, 1999, at American Type Culture Collection (ATCC), 10801 University Blvd., Manassas, Va. 20110-2209, USA and having the designation ATCC 202202.

The contents of each of the references cited herein are hereby incorporated by reference in their entirety.

The *P. corrugata* strains may be formulated with a variety of delivery media to produce bacterial inocula, that may be applied as either a dry powder or liquid suspension. Examples are included herein using 1% hydroxypropyl methylcellulose HPMC) with a minimal medium, in liquid and desiccated formulations. However any supporting nutrient media or broth can be used. A supporting nutrient medium is any medium that maintains the strain in an effective capacity for delivery. Delivery media can appropriately be minimal or defined, or complete or undefined nutrient media or substrate. However, the complete or undefined media may not be appropriate for desiccated formulations of these bacteria. We have observed that cultures grown in complete or rich media did not survive desiccation. The formulations may be introduced into the soil or may be applied to seeds, plant surfaces or portions of plants, such as roots, stems, leaves, and fruit, or plant parts may be dipped into the formulations or bacterial suspensions, to treat the plants.

Seeds are ideal delivery vehicles for biological control agents that act against seed and seedling diseases. Many problems associated with the failure of introduced microorganisms to colonize roots and persist in the rhizosphere can be avoided. Seeds also excrete nutrients during germination that may benefit biological control agents in the spermosphere. Formulations of the present invention can be applied to and dried on seeds. The long shelf life of seeds treated with formulations of the present invention can accommodate variations in grower planting schedules. *P. corrugata* seed treatment has not been shown to adversely affect seedling emergence and plant performance.

Also encompassed by this invention is a method of identifying and selecting desiccation tolerant strains of bacteria and a method of producing the desiccated formulations of the identified strains. The method comprises, in general, culturing the bacteria in a defined minimal nutrient broth medium containing a single carbon source (MMSC) for a minimum of approximately 24 hours. By defined media it is meant any media of known chemical composition. The minimal nutrient broth medium comprises at least a phosphate buffer, nitrogen, magnesium and the single carbon source. The carbon source selected in the examples below include galactose and dextrose, but, depending on the bacteria and conditions desired, other carbon sources may be tested and appropriately selected, in a like fashion, as described herein. After the culturing of the bacteria for 24 hours, samples of the MMSC cultures are dried. The dried samples are then rehydrated and plated, using a complete nutrient substrate. By complete nutrient substrate it is meant any substrate or media that contains undefined nutrients necessary to support the bacteria in a non-stressed manner. Typically an undefined medium and/or substrate contains at least one component that does not have a precise chemical definition. Undefined components are typically organically derived such as peptone, tryptone, yeast extract, etc. Examples of undefined media include TZC (Kelman 1954) medium and Luria-Bertani (LB) medium, both described further in Materials and Methods, below. The next step comprises identifying which strains have a high rate of survival by comparing the rate of survival of the rehydrated samples to the rate of survival of the control bacteria that have not been dried cultured in the same minimal nutrient broth and selecting the strains having a high rate of survival. In the case of the novel strains of *Pseudomonas corrugata* of the present invention, the composition comprising the desiccated strains and the delivery medium has a long shelf life and is suitable for delivering the bacteria to plants for effective control of plant pathogens.

Selected strains can then be applied on seeds as liquid coats or as dusts. Bacteria may be diluted in a 0.5 to 2% hydroxypropyl methylcellulose solution and used directly to coat seeds. Bacteria may also be mixed with inert carriers, dried, ground to a fine powder, and applied to seeds. By inert carriers, we mean any material that does not biologically react with the bacteria and have friability properties suitable for production of a powder-like material. Examples of inert carrier materials include talc, silica, fir bark, perlite, vermiculite, alginate, and clay.

MATERIALS AND METHODS

Bacterial Growth Media

All bacterial growth media were prepared using glass-distilled water and sterilized by autoclaving prior to use. Bacterial samples were handled using standard laboratory aseptic techniques. Media and other materials used are described below.

TZC (Kelman, Phytopatholgy, 44:693–695 1954)

MGY (Mannitol-Glutamate-Yeast): Mannitol 10 g, L-glutamic acid 2 g, $KH_2PO_4$ 0.5 g, NaCl 0.2 g, $MgSO_47H_2O$ 0.2 g, Yeast Extract 0.25 g, per liter water, pH 7.0.

PDA (potato dextrose agar): Available commercially from DIFCO Co., Detroit, Mich.

LB (Luria-Bertani) Medium: Tryptone 10 g, Yeast Extract 5 g, NaCl 5 g, per liter water, pH 7.2. Agar 15 g/l when needed for plates, 7 g/l for top agar.

MMSC (minimal medium single carbon source): $K_2HPO4$, 7 g; $KH_2PO_4$, 2 g; $MgSO_47H_2O$, 0.1 g; $(NH_4)_2SO_4$, 1 g; carbon source, 10 g; and agar, 15 g, per liter $H_2O$, pH 7.

CMA (Corn Meal Agar): Available commercially from DIFCO Co., Detroit, Mich.

NBY (Nutrient Broth-Yeast): Nutrient broth 8 g, yeast extract 2 g, agar 15 g; after autoclaving add: 1 M $K_2HPO_4$- $KH_2PO_4$ stock 10 ml, 25% dextrose stock 10 ml, 1 M $MgSO_47H_2O$ 1 ml, pH 7.

HPMC (hydroxypropyl methyl cellulose): 2% by weight dissolved in water and autoclaved prior to use.

Talc-1% HPMC: Talc with 1% by weight, dry hydroxypropyl methyl cellulose used as a carrier for dry formulations of *P. corrugata*. Autoclaved twice prior to use.

MMSC-HPMC: a 50:50 mix of MMSC and HPMC

MMSC-HPMC-TALC: 40 ml of MMSC added to 100 g of Talc-1% HPMC

Bacterial Cultivation

All bacterial genera and strains are part of the culture collection of Dr. Wesley W. C. Chun, Department of Plant, Soil and Entomological Sciences, University of Idaho, Moscow, Id. TZC agar plates were used to maintain culture purity and for monitoring bacterial populations of *P. corrugata* in all tests. MGY was used to evaluate isolates of *P. corrugata* for antibacterial activity. Antifungal activities were determined using PDA or CMA. LB or NBY agar plates were used to maintain all other test bacteria. LB top agar was used to construct lawns of test bacteria. MMSC served as the base medium for production of liquid and talc formulation of *P. corrugata*.

Fungal Cultivation

All fungal cultures are part of the culture collection of Dr. Wesley Chun, Department of Plant, Soil, and Entomological Sciences, University of Idaho, Moscow, Id. Cultures were maintained on either PDA or CMA.

Standard aseptic technique and sanitary procedures can be used in the handling of all the mentioned microbes. The following examples are provided for illustrative purposes and to further the understanding of the invention, and are not intended to limit the scope of the invention.

EXAMPLE 1

Isolation of *P. corrugata* Strains

Tomato plants that displayed pith necrosis symptoms were disinfected in a 10% bleach solution for 5 minutes. Small (2 mm×2 mm×4 mm) pieces of infected tissue were excised with a sterile scalpel and macerated in 200 microliters of sterile water. The suspension was streaked on TZC agar plates and observed for bacterial colonies with morphological features typical of *P. corrugata*. Suspected isolates were inoculated by syringe injection into stems of 7-week-old tomato seedlings and observed for the production of pith necrosis after 2 weeks. Eleven isolates were obtained. It was noted that colony characteristics varied widely between pathogenic isolates. Most isolates produced a bright green pigment while other isolates were white.

EXAMPLE 2

In vitro Bacterial Inhibition Assays

Isolates of *P. corrugata* were spotted on MGY agar plates and incubated at 26° C. for 1 to 2 days prior to testing.

Cultures were killed by exposure to chloroform vapors for 1 hr and aired for 1 hr. Top agar bacterial suspensions of test bacteria were poured over the chloroform-killed *P. corrugata* test plates. Growth inhibition zones were recorded after 2 to 7 days of growth. Table 1 relates the results obtained.

EXAMPLE 3

In vitro Fungal Inhibition Assays

All assays were performed on PDA. For slow growing fungi, fungal cultures were inoculated and grown for 2 to 6 days before inoculation of *P. corrugata* isolates. Both bacteria and fast growing fungi were inoculated on the same day. Normally, bacterial isolates were spotted 1 cm away from the leading edge of the fungal colony or from the transfer block. Observations were recorded over a 7 day interval. Table 2 provides a list of fungi that were tested. All were inhibited by isolates 0782-6 and 0683-32. Other isolates varied in their ability from moderate suppression to no suppression.

TABLE 1

Bacterial genera and strains that are susceptible or are not susceptible to antimicrobial metabolites of *Pseudomonas corrugata.*

| Bacterial strain |
|---|
| Strains inhibited by *P. corrugata* |
| *Bacillus cereus* |
| *Bacillus licheniformis* |
| *Bacillus subtilis* |
| *Clavibacter michiganensis* subsp. Insidiosus |
| *Clavibacter michiganensis* subsp. Michiganensis |
| *Clavibacter michiganensis* subsp. Sepedonicus |
| *Erwinia quercina* |
| *Micrococcus luteus* |
| *Pseudomonas cepacia* |
| *Pseudomonas syringae* pv. Pisi |
| Strains not inhibited by *P. corrugata* |
| *Agrobacterium tumefaciens* |
| *Pseudomonas syringae* pv. Atropurpurea |
| *Pseudomonas syringae* pv. Glycinea |
| *Pseudomonas syringae* pv. Marginalis |
| *Pseudomonas syringae* pv. Phaseolicoia |
| *Pseudomonas syringae* pv. Syringae |
| *Xanthomonas campestris* pv. Campestris |

TABLE 2

Fungal strains inhibited by *Pseudomonas corrugata.*

| Fungal strain |
|---|
| *Ascochyta fabae* f. sp. lentis |
| *Ascochyta pisi* |
| *Ascochyta rabiei* |
| *Botrytis cinerea* |
| *Fusarium oxysporum* f. sp. ciceris |
| *Fusarium sambucinum* |
| *Gaeumannomyces graminis* var. tritici |
| *Helminthosporium solani* |
| *Mycosphaerella pinodes* |
| *Phoma medicaginis* var. pinodella |
| *Pythium irregulare* |
| *Pythium sylvaticum* |
| *Pythium ultimum* |
| *Pythium ultimum* var. ultimum |
| *Pythium ultimum* var. sporangiiforum |
| *Rhizoctonia solani* |
| *Sclerotinia sclerotiorum* |

EXAMPLE 4

Competitive Inhibition Assays

Standard techniques, well known in the art were used to introduce both *C.* m. subsp. *sepedonicus* and *P. corrugata* into eggplant and potato stems. *C.* m. subsp. *sepedonicus* cultures were grown for 2 days in NBY broth at 24° C. *P. corrugata* cultures were grown for 24 h at 24° C. Bacteria were harvested by centrifugation and resuspended in sterile saline (0.85% NaCl) and adjusted spectrophotometrically to 0.5 absorbence units at 600 nm. Five microliters of bacterial inocula were applied to wounds in leaf axils created by insertion of a dissecting needle to a depth of 4 mm. Bacterial populations in the stem were monitored over time by dilution plating on TZC and NBY supplemented with Spectinomycin (50 $\mu$g/ml) for enumeration of *P. corrugata* and *C.* m. subsp. *sepedonicus,* respectively. Inoculation of whole cultures and cell free culture filtrates were also compared in the eggplant studies.

FIG. 1 illustrates the suppressive effect of *P. corrugata* (whole culture and washed cells) and cell-free culture fluids on stem populations of *C.* m. subsp. *sepedonicus* in eggplants. With washed cells and whole cultures of *P. corrugata,* populations of *C.* m. subsp. *sepedonicus* declined from initial population of $10^4$ colony forming units/gram (CFU/g) of stem tissue to approximately 10 CFU/g. In several isolations, *C.* m. subsp. *sepedonicus* was not recovered. When *C.* m. subsp. *sepedonicus* was inoculated alone, population increased to over $10^8$ CFU/g at four weeks. When cell-free culture fluids were included in the inoculum, populations also increased but appeared to be slightly delayed. In plants inoculated with *P. corrugata* alone, populations of $10^8$ CFU/g were recovered throughout the experiment. In these plants, no symptoms were observed. However, in the plants inoculated with *C.* m. subsp. *sepedonicus* alone and with cell-free culture fluids of *P. corrugata,* the leaf adjacent to the inoculation site had noticeable chlorosis. Thus, *P. corrugata* can maintain high populations in non-host plants and suppress growth of *C.* m. subsp. *sepedonicus* in the occupied sites.

Similar results were obtained in both Russet Burbank and Shepody potato plants. FIGS. 2*a* and 2*b* are the results of one of the replicated experiments performed in Shepody and Russet Burbank potato plants, respectively. In all inoculations, no chlorosis was observed on the leaves adjacent to the inoculation site. However, high population of *C.* m. subsp. *sepedonicus* developed during the observation period when inoculated alone. In both potato cultivars, a chemically derived (from 0782-6) non-pathogenic (to tomatoes) mutant strain M1423, gave similar suppression of *C.* m. subsp. *sepedonicus* in Shepody. However, in Russet Burbank, M1423 did not appear to be as effective. In both Shepody and Russet Burbank, the parent strain 0782-6 showed strong in planta suppression of *C.* m. subsp. *sepedonicus.*

EXAMPLE 5

Formulation of Bacteria

1. Enhanced survival of *Pseudomonas corrugata*. Different carbon sources were used in MMSC broth for growth of *P. corrugata*. Aliquots of 24 hour old cultures were dried and bacterial survival measured by rehydration and dilution plating on TZC agar plates. Only dextrose and galactose supplemented MMSC media grown bacteria were tolerant of desiccation. Galactose was selected as the carbon source as bacterial survival was 1,000 to 10,000 times greater than dextrose grown cultures. Subsequent experiments showed that the addition of approximately 1% hydroxypropyl methylcellulose (HPMC) to liquid cultures increased survival. In comparison tests, a 1% HPMC-talc base containing 4 ml of bacterial culture consistently had the highest survival rate when compared to combinations of talc, silica, and HPMC-silica, mixed with varying amounts of HPMC and bacteria. Although the 1% HPMC-talc formulations had the highest survival rates, other percentages of HPMC and other appropriate delivery media may be used. Other appropriate delivery media include, but are not limited to other percentages of HPMC, talc, silica, minimal media, defined media, complete nutrient media and/or substrate, and varying combinations of the same. The 1% HPMC-talc formulation described herein can be air dried, pulverized and sized through sieving screens. Particle sizes greater than 250 $\mu$m and smaller than 1410 $\mu$m yielded the greatest percentage of surviving bacteria. Approximately $10^6$ colony forming units (CFU) per gram formulation are recoverable after 86 days of storage.

2. Formulation evaluation for disease control. Survival of *P. corrugata* on cut seed potato. The talc formulation described above was applied on cut surfaces of potatoes (1.5 g/tuber) and populations monitored over time by dilution plating on agar media. Four tubers were assayed weekly by excising three plugs with a No. 3 cork borer. Recoverable populations averaged $1.1\times10^6$, $6.5\times10^6$, and $4.7\times10^6$ CFU/g tissue on weeks 1, 2, and 3, respectively. No deleterious effects were observed on all treated tubers. The talc formulation could thus be used on cut seed potato to introduce stable populations of *P. corrugata*.

EXAMPLE 6

Field Suppression of Silver Scurf Disease

Russet Burbank seed potato heavily infected with *Helminthosporium solani* were treated with 1% HPMC liquid and talc formulations of *P. corrugata*, and with Tops-MZ (2.5% thiophante-methyl, 6% mancozeb, Gustafson, Inc., 1400 Preston Rd, Suite 400, Plano, Tex. 75093 USA). Initial populations in the 1% HPMC liquid and talc formulations were $4.7\times10^8$ CFU/ml and $1\times10^6$ CFU/g, respectively. Certified Russet Burbank seed potatoes that were relatively free of silver scurf, were used as healthy controls. Infected seeds with no treatment were used as positive controls. Stand counts with the 0782-6:HPMC-talc and liquid 0782-6:HPMC formulations were slightly better than other treatments, as shown in the results in Table 3. At 11-weeks, at least 150 tubers were harvested from each treatment and evaluated for silver scurf by incubation in moist chambers. The majority of the harvested tubers from the Tops-MZ treatment, strain 0782-6 treatments (both HPMC-talc and 1% HPMC formulations), and the healthy seed control fell into the 'Slight' category (less than five lesions per tuber) (Table 3). Within this category, 91% of the tubers from the Tops-MZ treatment had no symptoms as compared to 42% of the 0782-6:HPMC-talc and 23% of the 0782-6:HPMC treatments. A significantly lower percentage of tubers were considered slightly infected with the infected tuber and the 1090-11 negative controls. A similar pattern was also observed when comparing tubers that have between five lesions to 10% of the tuber surface affected. At the other disease levels Pc 0782-6:HPMC-talc treatment was similar to that of the healthy seed control treatment. This treatment may also be better than the 1% HPMC liquid formulation, 1090-11, and the infected tuber controls.

Under field conditions, *P. corrugata* treatment suppressed silver scurf early in the growing season. However, significant reduction of silver scurf was not observed at the end of the growing season, as shown in Table 4. No significant differences were observed with the *P. corrugata* treatments and infected tuber controls (tubers that have 10% or less of the surface affected). There appears to be a slight, but statistically not significant, decrease in the number of tubers that have between 10% and 50% of the surface affected with strain 0782-6 treatments. Thus, most of the antagonistic effect against *H. solani* occurred early in the growing season. Warmer temperatures late in the growing season may not be supportive of maintaining high populations of *P. corrugata*.

Greenhouse experiments. An expanded set of greenhouse experiments were conducted. Seed potato were inoculated with *H. solani* five weeks before applying treatments. Seed pieces were treated with bacterial formulations and Tops-MZ as above. However, careful control produced talc formulations of $1.9\times10^6$ CFU/g (0782-6), $2.7\times10^7$ CFU/g (1090-11), and $5.8\times10^4$ CFU/g (M1423). Liquid 1% HPMC formulations ranged from $10^8$ to $10^9$ CFU/ml for the *P. corrugata* isolates. Treatment rates were 24 oz/100 lb. for talc formulations, 16 oz/100 lb. for 1% HPMC formulations, and 16 oz/100 lb. for Tops-MZ. Five seed potatoes (whole) were planted for each replication. Each treatment was replicated three times. Treated tubers were planted in field soil in nine-inch diameter pots and grown in the greenhouse. At the end of the season, tubers were harvested and assayed for silver scurf as described above.

With most *P. corrugata* treatments, the number of tubers with little or no scurf was increased when compared to the infected tuber control. The carrier materials also seemed to have a positive effect. It is possible that the carriers aided the establishment of other resident micro-organisms present in the soil. Similar relationships are observed when results are compared in the other disease severity levels. However, these differences were not statistically significant. Thus, the greenhouse data also suggests that *P. corrugata* treatment alone may not be effective the entire cropping season.

TABLE 3

The effect of *P. corrugata* and Tops-MZ seed treatment on stand counts and daughter tubers with different levels of silver scurf disease 11 weeks after planting.

| Treatment | Stand (32 d) | Disease symptoms[1] (percent of all tubers tested) | | | |
|---|---|---|---|---|---|
| | | Slight | Moderate | Heavy | Severe |
| Pc 0782-6 HPMC-Talc | 24.0 a2 | 91[3] ab | 8 ab | 1 a | 0 |
| Pc 0782-6 1% HPMC | 24.0 a | 83 ab | 17 ab | 0 a | 0 |
| Pc 1090-11 HPMC-Talc | 23.3 ab | 63 b | 30 b | 7 a | 0 |
| Infected tuber control | 22.8 ab | 63 b | 32 b | 5 a | 0 |
| Tops-MZ | 21.8 ab | 100 a | 0 a | 0 a | 0 |
| Healthy tubers | 20.8 b | 92 ab | 8 a | 0 a | 0 |

[1]Slight = 0 to 5 lesions per tuber; Moderate = several lesions with up to 10% of the tuber affected; Heavy = greater than 10% but less than 50% of the tuber surface affected, some shrinking possible; and severe = greater than 50% of the tuber surface affected by silver scurf with shrinking of the tuber.
[2]Data with the same letter are not significantly different using Tukey's Studentized Range (HSD) Test (p>0.10).
[3]Means in each category are percentages calculated from the tubers rated in each category divided by the total number of tubers observed. At least 150 tubers were evaluated for each treatment.

TABLE 4

The effect of *P. corrugata* and Tops-MZ seed treatment on daughter tubers with different levels of silver scurf after harvest.

| Treatment | Disease symptoms[1] (percent of all tubers tested) | | | |
|---|---|---|---|---|
| | Slight | Moderate | Heavy | Severe |
| Pc 0782-6 HPMC-Talc | 16[2] b[3] | 51 b | 28 b | 5 a |
| Pc 0782-6 1% HPMC | 15 B | 57 b | 28 b | 0 a |
| Pc 1090-11 HPMC-Talc | 10 B | 50 b | 35 b | 5 a |
| Infected tuber control | 14 B | 41 b | 39 b | 6 a |
| Tops-MZ | 90 A | 10 a | 0 a | 0 a |
| Healthy tubers | 68 A | 30 ab | 2 a | 0 a |

[1]Slight = 0 to 5 lesions per tuber; Moderate = several lesions with up to 10% of the tuber affected; Heavy = greater than 10% but less than 50% of the tuber surface affected, some shrinking possible; and severe = greater than 50% of the tuber surface affected by silver scurf with shrinking of the tuber.
[2]Means in each category are percentages calculated from the tubers rated in each category divided by the total number of tubers observed. At least 150 tubers were evaluated for each treatment.
[3]Data with the same letter are not significantly different using Tukey's Studentized Range (HSO) Test (p>0.10).

TABLE 5

The effect of *P. corrugata* and Tops-MZ seed treatment on daughter tubers with different levels of silver scurf after growth in the greenhouse.

| Treatment | Disease symptoms[1] (percent of all tubers tested) | | | |
|---|---|---|---|---|
| | Slight | Moderate | Heavy | Severe |
| Pc 0782-6 HPMC-Talc | 30[2] B[3] | 58 a | 10 a | 2 a |
| Pc 0782-6 1% HPMC | 54 Ab | 37 a | 10 ab | 0 a |
| Pc 1090-11 HPMC-Talc | 10 B | 66 a | 15 ab | 2 a |
| Pc 1090-11 1% HPMC | 33 Ab | 58 a | 9 a | 0 a |
| Pc M1423 HPMC-Talc | 39 Ab | 38 a | 15 ab | 7 a |
| Pc M1423 1% HPMC | 28 Ab | 62 a | 10 a | 0 a |
| HPMC-Talc | 27 Ab | 50 a | 20 ab | 3 a |
| 1% HPMC | 27 Ab | 53 a | 16 ab | 5 a |
| Infected tuber control | 14 b | 46 a | 38 b | 11 a |
| Tops-MZ | 74 A | 23 a | 3 a | 0 a |
| Healthy tubers | 56 Ab | 35 a | 7 a | 2 a |

[1]Slight = 0 to 5 lesions per tuber; Moderate = several lesions with up to 10% of the tuber affected; Heavy = greater than 10% but less than 50% of the tuber surface affected, some shrinking possible; and severe = greater than 50% of the tuber surface affected by silver scurf with shrinking of the tuber.
[2]Means in each category are percentages calculated from the tubers rated in each category divided by the total number of tubers observed. At least 150 tubers were evaluated for each treatment.
[3]Data with the same letter are not significantly different using Tukey's Studentized Range (HSD) Test (p>0.10).

EXAMPLE 7

Suppression of Pythium Root Rot of Wheat

In these experiments isolates of *P. corrugata* were applied as a 1% HPMC seed coat on Madsen and Stephens wheat seed. Treated seed were then planted in non-sterilized field soil artificially infested with oospores of *Pythium ultimum* and *P. irregulare* to obtain approximately 100 oospores per gram. Plants were watered daily and data recorded after 14 days. Carboxin and Metalaxyl treated seeds were included as comparison controls.

A significant increase in seedling emergence was observed when seeds were treated with strain 0782-6 on both Madsen (Table 6) and Stephens (Table 7) wheat when compared to controls. Metalaxyl, which is known to inhibit *Pythium* spp. was second. Corresponding increases in plant height, root length, and fresh weights were observed. Most noticeable was the lack of root rot symptoms on roots with the 0782-6 treatment. *P. corrugata* strain 1090-11 in agar plate tests cannot suppress growth of Pythium. As expected, performance of this strain was poor and statistically fell into or near the groups containing the controls.

TABLE 6

Effect of seed treatment with *P. corrugata* 0782-6 and 1090-11 on Pythium root rot of Madsen wheat in greenhouse tests using non-sterilized field soil[a]

| Pythium spp. | Seed treatment | EM % | DR (0–6) | HT (cm) | RL (cm) | PFW (mg) | RFW (mg) |
|---|---|---|---|---|---|---|---|
| P. ultimum var. ultimum | None | 30 | 5.1d[b] | 27.7c | 4.4d | 340d | 13c |
| | 1.5% HPMC | 60 | 4.9d | 22.4e | 7.1c | 340d | 14c |
| | 1090-11 + 1.5% HPMC | 50 | 5.2d | 23.2d | 4.7d | 380c | 13c |
| | Carboxin | 70 | 4.2c | 27.4c | 8.5b | 400c | 21b |
| | Metalaxyl | 80 | 2.9b | 28.6b | 8.4b | 440b | 20b |
| | 0782-6 + 1.5% HPMC | 100 | 0.7a | 30.6a | 12.3a | 500a | 37a |
| P. irregulare | None | 50 | 4.5d | 22.7e | 6.3d | 340e | 13b |
| | 1.5% HPMC | 70 | 4.3d | 29.6b | 8.9b | 500b | 15b |
| | 1090-11 + 1.5% HPMC | 80 | 3.8c | 26.4d | 8.4c | 440d | 14b |
| | Carboxin | 100 | 2.2b | 26.2d | 8.4c | 470c | 15b |
| | Metalaxyl | 100 | 2.1b | 28.7c | 8.5c | 500b | 15b |
| | 0782-6 + 1.5% HPMC | 100 | 0.4a | 35.7a | 15.6a | 620a | 34a |

[a]EM = emergence (%), sum of 10 replicates. HT = plant height, RL = root length, DR = disease rating (0 = healthy and 6 = seed dead), PFW = plant fresh weight, RFW = root fresh weight. Mean of 10 replicates 15 days after planting based on the following formulas: DR = Σ(DRs from 10 replicates) / 10, HT = Σ (HTs from N growing replicates) / N (cm), RL = Σ(RLs from N growing replicates) / N (cm), PFW = Σ(PFWs from N grow replicates) / N (mg), RFW = Σ(RFWs from N growing replicates) / N (mg).
[b]Means in the same column followed by a different letter are significantly different, P < 0.05, according to Fisher's Protected LSD. Data for *P. ultimum* and *P. irregulare* inoculations were analyzed separately.

TABLE 7

Effect of seed treatment with *P. corrugata* 0782-6 and 1090-11 on Pythium root rot of Stephens wheat in greenhouse tests using non-sterilized field soil.[a]

| Pythium spp. | Seed treatment | EM % | DR (0–6) | HT (cm) | RL (cm) | PFW (mg) | RFW (mg) |
|---|---|---|---|---|---|---|---|
| P. ultimum var. ultimum | None | 40 | 5.6d[b] | 22.2e | 4.3e | 200c | 7.0d |
| | 1.5% HPMC | 50 | 4.6c | 26.3b | 8.0b | 360a | 19b |
| | 1090-11 + 1.5% HPMC | 60 | 4.5c | 25.5c | 5.9d | 300b | 14c |
| | Carboxin | 60 | 4.3c | 24.8d | 7.6c | 320b | 15c |
| | Metalaxyl | 80 | 2.8b | 26.5b | 7.6c | 360a | 16c |
| | 0782-6 + 1.5% HPMC | 90 | 1.3a | 29.6a | 10.4a | 370a | 26a |
| P. irregulare | None | 30 | 5.5e | 26.2b | 6.1d | 290d | 9.0d |
| | 1.5% HPMC | 70 | 4.4c | 25.7c | 5.4e | 250e | 14c |
| | 1090-11 + 1.5% HPMC | 60 | 4.8d | 23.2d | 6.7d | 400c | 15c |
| | Carboxin | 70 | 4.2c | 26.3b | 7.4c | 500b | 19b |
| | Metalaxyl | 90 | 2.0b | 26.6b | 11.1b | 320d | 20b |
| | 0782-6 + 1.5% HPMC | 100 | 0.1a | 27.1a | 13.a | 580a | 35a |

[a]EM = emergence (%), sum of 10 replicates. HT = plant height, RL = root length, DR = disease rating (0 = healthy and 6 = seed dead), PFW = plant fresh weight, RFW = root fresh weight. Mean of 10 replicates 15 days after planting based on the following formulas. DR = Σ(DRs from 10 replicates) / 10, HT = Σ (HTs from N growing replicates) / N (cm), RL = Σ(RLs from N growing replicates) / N (cm), PFW = Σ(PFWs from N growing replicates) / N (mg), RFW= Σ(RFWs from N growing replicates) / N (mg).
[b]Means in the same column followed by a different letter are significantly different, P < 0.05, according to Fisher's Protected LSD. Data for *P. ultimum* and *P. irregulare* inoculations were analyzed separately.

EXAMPLE 8

Genetic Traits

Chemical and transposon mutagenesis of *P. corrugata* strain 0782-6 resulted in the identification of mutants that were no longer pathogenic in tomatoes. Standard methods using ethylmethansulfonate were used to generate chemically induced mutants. A mini-Tn5 strain of *Escherichia coli*, E17-1(λpir)(pUT:Km) (de Lorenzo and Timmis, 1994) was used to generate transposon mutants. The method for transposon mutagenesis was modified from Herrero et al. (Hererro et al., 1990). One-milliliter of each culture was centrifuged and resuspended in fresh LB broth. A sterile 0.45 $\mu$m (25 mm diameter) membrane filter was placed on an LB agar plate to which 30 $\mu$l of the donor [E17-1λpir(pUT:Km)] was added and spread over the filter. Twenty microliters of the recipient (*P. corrugata* strain 0782-6) was layered over the donor and the plate incubated overnight at 27° C. The filter was transferred to a microfuge tube with 1 ml of 10 mM $MgSO_4$ and vortexed to release the cells. The filter was removed, the cells pelleted by centrifugation, and resuspended in 1 ml of 10 mM $MgSO_4$. Washed cells were diluted 10-fold and 100 $\mu$l of each dilution was plated on minimal media with sucrose (MMS), composed of sucrose, 10 g; $K_2HPO_4$, 7 g; $KH_2PO_4$, 2 g; $MgSO_4.7H_2O$, 0.1 g; $(NH_4)_2SO_4$, 1 g per liter of distilled water (pH 7) and amended with 50 μg/ml kanamycin ($MMSKm_{50}$). The plates were incubated-at 27° C. for 2 days and colonies were picked onto fresh plates of $MMSKm_{50}$.

*P. corrugata* mutants were grown on $MMSKm_{50}$ and wild-type *P. corrugata* (strains 0782-6 and 1090-11) on MMS without antibiotic selection. Each bacterium was transferred to nutrient broth-yeast extract (NBY) agar plates using a sterile toothpick. Nine mutants were tested on each plate with at least 25 mm between colonies. Plates were incubated for 16 hr at 27° C. *P. corrugata* mutants were killed by 30 min. exposure to 3 $cm^2$ pieces of filter paper soaked in chloroform, followed by 90 min. of airing to remove the chloroform. *Clavibacter michiganensis* subsp. *sepedonicus* isolate Cms9 was used as an indicator for antibacterial activity. *C. m.* subsp. *sepedonicus* was grown in 10 ml cultures of NBY broth. After 48 hr growth at 26° C., 500 μl of the bacterial suspension was combined with 4.5 ml LB top agar (0.7%) and overlaid onto plates containing killed colonies of *P. corrugata*. Plates were incubated for 4 to 6 days and evaluated for inhibition. Prospective mutants with reduced activity were retested in triplicate.

Mutants were screened for antifungal activity using *Rhizoctonia solani* (AG-3, R1131) as an indicator. *P. corrugata* mutants and wild-type strains were grown as described above. Each bacterium was replica-plated onto potato dextrose agar (PDA, DIFCO) plates with 48 colonies per plate in a 6×8 arrangement. *R. solani* was grown on PDA and three-day-old cultures were used for antifungal assays. Plugs from the outer mycelial growth were removed using a #2 cork borer (5 mm diameter) and placed between 4 colonies of *P. corrugata* so that 12 plugs of *R. solani* were on each PDA plate. Plates were incubated for three days at 27° C. and observed for inhibition zones. The distance between the advancing edge of the mycelium and the bacterial colony of putative mutants were compared to inhibitory regions observed with the antagonistic strain of *P. corrugata* (0782-6). Mutants identified as having reduced activity were retested in duplicate by placing four spots (two isolates per plate) 1 cm away from a plug of *R. solani*. Plates were incubated and observed as described above.

*P. corrugata* mutants Were grown overnight in 2.5 ml MMS broth at approximately 21° C. with shaking. Bacteria were harvested by centrifugation and resuspension in 2.5 ml 0.85% saline solution. Tomato plants grown under greenhouse conditions were inoculated by making puncture wounds to the leaf axil with a sterile dissecting needle. Bacteria were applied by micropipetting 5 μl of bacterial suspension onto the wound. Plants were grown for two additional weeks, watering daily and fertilizing with 200 ppm N-P-K (14-15-16) weekly. The stem near-the sight of inoculation was cut open using a scalpel and examined for water soaking and necrosis. Bacterial isolates testing negative were reinoculated into five plants to confirm phenotype.

Sixteen isolates were randomly selected from the list of mutants and DNA was isolated and purified by CsCl purification (0.9 g CsCl/ml) with 16 and 8 hr spins at 60K and 65K, respectively. The transposon was excised and extracted from an agarose gel. A probe was labeled with biotin by random priming with Biotin-High Prime (Boehringer Mannheim). Southern hybridization was performed at 65° C. overnight and detection the following day using Southern-Light (TROPIX, Inc., Bedford, Mass.) detection for non-radioactive biotin labeled probes.

Mutagenesis with the mini-Tn5 transposon generated 2,947 mutants of *P. corrugata* strain 0782-6. Antibacterial and antifungal mutants were obtained with varying phenotypes listed in Table 8. Zone of inhibition measurements demonstrated that mutants 28–37 and 28–39 were most like 1090-11 (wild-type, non-antagonist). Four isolates were also identified with reduced pathogenicity that retained wild-type antimicrobial activity.

The phenotypes can be grouped into nine categories shown in Table 8. The most common antimicrobial mutation resulted in complete loss of both clear and turbid zones (M8), observed with *C. m.* subsp. *sepedonicus,* or reduced clear and no turbid zones (M5). A reduced antifungal activity was also observed for both mutant types with a greater reduction in activity with the M8 mutation.

Thus it appears that pathogenicity and antimicrobial activities are not linked traits. Non-pathogenic derivatives that can be used as biological control agents are possible, such as 1090-11.

TABLE 8

Summary of *Pseudomonas corrugata* (strain 0782-6) mutants with reduced antimicrobial activity or tomato pathogenicity[y].

| Mutant type | Antibacterial activity[z] | | Antifungal activity | Tomato pathogenicity | Number of mutants | Isolate numbers |
|---|---|---|---|---|---|---|
| | Clear zones | Turbid zones | | | | |
| M1 | + | + | ++ | + | 2897 | — |
| M2 | + | − | ++ | + | 3 | 10–47, 26–1, 52–39 |
| M3 | + | − | + | + | 1 | 26–44 |
| M4 | +/− | + | ++ | + | 6 | 15–29, 26–14, 30–25, 31–2, 31–4, 48–39 |
| M5 | +/− | − | + | + | 15 | 1–1, 5–1, 5–14, 5–40, 6–11, 10–42, 14–11, 14–35, 15–1, 17–29, 20–37, 21–31, 29–7, 30–41, 49–34 |
| M6 | − | + | ++ | + | 5 | 26–7, 28–27, 38–14, 40–18, 47–7 |
| M7 | − | + | + | + | 2 | 16–36, 48–40 |
| M8 | − | − | +/− | + | 14 | 13–15, 15–2, 16–43, 18–11, 25–12, 27–8, 27–14, 27–45, 28–37, 28–39, 28–44, 29–38, 32–12, 37–28 |
| M9 | + | + | ++ | − | 4 | 7–34, 9–1, 27–27, 53–45 |

TABLE 8-continued

Summary of *Pseudomonas corrugata* (strain 0782-6) mutants with reduced antimicrobial activity or tomato pathogenicity[y].

| Mutant type | Antibacterial activity[z] | | Antifungal activity | Tomato pathogenicity | Number of mutants | Isolate numbers |
|---|---|---|---|---|---|---|
| | Clear zones | Turbid zones | | | | |

[y]*P. corrugata* strain 0782-6 had an antimicrobial and pathogenicity phenotype similar to mutant type M1, and strain 1090-11 has reduced antibacterial clear zones, lack turbid zones and antifungal activity, and is pathogenic in tomato plants.
[z]Antibacterial activity was determined as either clear zones or turbid zones.

Whereas particular embodiments of the invention have been described hereinabove, for purposes of illustration, it will be evident to those skilled in the art that numerous variations of the details may be made without departing from the invention as defined in the appended claims.

The novel strains of *Pseudomonas corrugata*, particular formulations and processes of the present invention are not limited to the descriptions of specific embodiments presented hereinabove, but rather the descriptions and examples herein of the present invention should be viewed in terms of the claims that follow and equivalents thereof. While some of the examples and descriptions above include some conclusions about the way the strains may function, the inventor is not intended to be bound by those functions, but puts them forth only as possible explanations. Further, while the invention has been described in conjunction with several such specific embodiments, it is to be understood that many alternatives, modifications, and variations will be apparent to those skilled in the art in light of the foregoing detailed descriptions. Accordingly, this invention is intended to embrace all such alternatives, modifications, and variations which fall within the spirit and scope of the appended claims.

I claim:

1. A method for evaluating desiccation tolerance of strains of bacteria comprising: culturing samples of bacteria in minimal nutrient broth medium containing a single carbon source (MMSC) for a minimum of approximately 24 hours; drying the samples of bacteria cultured in MMSC; rehydrating the samples on a complete nutrient substrate; and determining the survival rates of bacteria in the samples by comparing the rate of survival of bacteria in the rehydrated samples to the rate of survival of the bacteria in a control sample that has not been dried.

2. The method of claim 1 wherein said single carbon source is selected from the group consisting of dextrose and galactose.

3. The method of claim 1, further comprising selecting the sample with the highest survival rate.

4. The method of claim 3, further comprising repeating the selection method of claim 3 at least once on the selected sample.

5. The method of claim 1, wherein said bacteria is of the genus Pseudomonas.

6. The method of claim 5, wherein said bacteria is selected from the group consisting of *Pseudomonas corrugata* 0782-6, *Pseudomonas corrugata* 0683-32 and *Pseudomonas corrugata* 1090-11.

7. The method of claim 1 further comprising repeating the process of claim 1 on the same samples of bacteria using a different single carbon source; and comparing the survival rates of the selected samples for each carbon source.

8. The method of claim 7, further comprising identifying the sample with the highest survival rate; and selecting the sample with the identified highest survival rate.

9. The method of claim 1, wherein the different single carbon source is selected from the group consisting of dextrose and galactose.

10. A method for selecting desiccation tolerant strains of bacteria comprising:
   a) culturing samples of bacteria in minimal nutrient broth medium containing a single carbon source (MMSC) for a minimum of approximately 24 hours;
   b) drying the samples of bacteria cultured in MMSC;
   c) rehydrating the samples on a complete nutrient substrate;
   d) identifying the sample with the highest survival rate by comparing the rate of survival to a control sample that has not been dried;
   e) selecting the sample with the identified highest survival rate; and
   f) repeating a) through e) on the selected sample until the survival rate does not increase with repeated selections.

11. The method of claim 10, further comprising repeating a) through f) at least once on the same samples of bacteria using an MMSC with at least one different single carbon source; comparing the survival rates of samples selected using different carbon sources; and identifying the carbon source that results in the sample with the highest survival rate.

* * * * *